United States Patent [19]
Rosenberg et al.

[11] Patent Number: 5,897,910
[45] Date of Patent: Apr. 27, 1999

[54] PRODUCTION OF COVERED TABLETS

[75] Inventors: Joerg Rosenberg, Ellerstadt; Werner Maier, Schifferstadt; Sven Grabowski, Ludwigshafen; Jörg Breitenbach, Mannheim, all of Germany

[73] Assignee: BASF Aktiengesellschaft, Ludwigshafen, Germany

[21] Appl. No.: 08/860,016

[22] PCT Filed: Dec. 22, 1995

[86] PCT No.: PCT/EP95/05118

§ 371 Date: Jun. 20, 1997

§ 102(e) Date: Jun. 20, 1997

[87] PCT Pub. No.: WO96/19963

PCT Pub. Date: Jul. 4, 1996

[30] Foreign Application Priority Data

Dec. 23, 1994 [DE] Germany .............................. 44 46 468

[51] Int. Cl.$^6$ ................ B05D 3/12; A61J 3/06; A61J 3/07

[52] U.S. Cl. .................. 427/2.14; 427/2.21; 427/358; 427/365; 427/366

[58] Field of Search .................... 427/2.14, 2.23, 427/2.22, 2.21, 358, 364, 365, 375, 366

[56] References Cited

U.S. PATENT DOCUMENTS

| | | |
|---|---|---|
| 2,513,852 | 7/1950 | Donofrio . |
| 4,154,636 | 5/1979 | Motoyama et al. ................ 156/285 |
| 4,289,795 | 9/1981 | Bogentoft et al. ................ 427/2.21 |
| 4,375,146 | 3/1983 | Chung ........................... 53/453 |
| 4,880,585 | 11/1989 | Klimesch et al. ................ 264/141 |
| 5,146,730 | 9/1992 | Sadek et al. .................... 53/454 |
| 5,192,548 | 3/1993 | Velasquez et al. ................ 424/443 |

*Primary Examiner*—Diana Dudash
*Attorney, Agent, or Firm*—Keil & Weinkauf

[57] ABSTRACT

The present invention is a process for the production of covered tablets by melt calendering in which the melt containing active ingredient is introduced between two sheets of the covering material into the molding rolls.

20 Claims, 1 Drawing Sheet

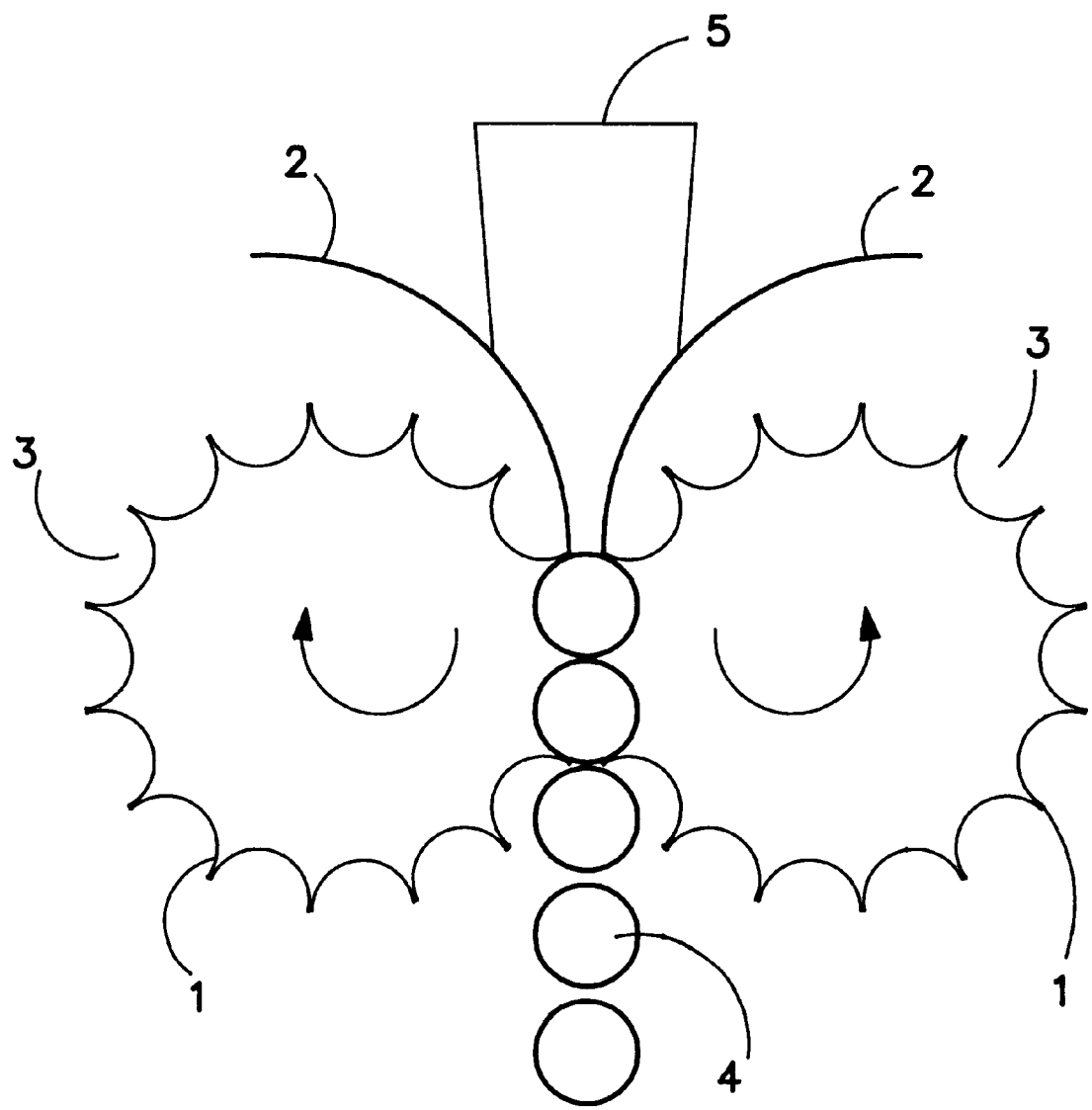

PRODUCTION OF COVERED TABLETS

The present invention relates to a process for the production of covered tablets by molding a melt which contains an active ingredient in a calender with counter-rotating molding rolls which have on their surface depressions for receiving and molding the tablet composition (melt calendering).

The production of tablets by calendering a melt containing an active ingredient is disclosed in DE-A 1 766 546 and U.S. Pat. No. 4,880,585. The basis of this process is the embedding of an active ingredient in a melt of a carrier, eg. fatty substances or water-soluble thermoplastic polymers. The melt is produced by melting the mixture of active ingredient, polymer and, where appropriate, other ancillary substances, for example in an extruder, and molding the melt in a downstream molding calender to give tablets, which harden on cooling. The molding calender comprises a pair of counter-rotating molding rolls which have on their surface engravings (depressions) which correspond to the shape of one half of the required tablet. The tablet molding takes place in the region of contact of the two rolls by combination of the tablet composition in one depression on one roll with that in the opposite depression on the other roll.

Most of the tablets on the market are produced as film-coated tablets, ie. a thin layer of water-soluble polymers is applied to the tablets in the last production step. This film-coating is often indispensable for various reasons, because, for example, a) a taste which is conferred by the active ingredients and/or ancillary substances used must be masked until the tablet reaches the stomach, b) the active ingredient used is unstable to, for example, light, moisture etc., c) the tablets require a colored coating for easier identification.

The protective layers (the coating) have to date been applied almost exclusively by spraying on solutions of water-soluble polymers (organic solvents and/or water) with simultaneous drying. Besides the film coating (layer thickness in the micrometer range) which is conventional nowadays, there is the sugar-coating process in which thick layers, which are sometimes in the millimeter range, of sugar-containing mixtures are applied. These widely used techniques are described in various textbooks (see H. Sucker, P. Fuchs, P. Speiser: Pharmazeutische Technologie; 2nd edition, G. Thieme Verlag Stuttgart (1991), pages 347–368).

If a coating was required over the tablets produced by melt calendering it was necessary to apply this coating in a separate step after the tablets had cooled. This took place in a conventional way, for example by spraying on in rotating drums, by the dip pipe process or in a fluidized bed etc.

The conventional processes for applying coating layers or for sugar coating all require comparatively very high energy input, because the solvents used in the spray solutions must be removed again rapidly after spraying onto the tablets. In addition, a coating process usually takes several hours because the spraying rate cannot be set as high as may be required.

The application of the coating in a separate step thus requires considerable expenditure of time, additional machinery and additional staff, which has marked effects on the production costs.

It is an object of the present invention to provide a process for the production of covered tablets by melt calendering in which covering of the tablets is possible in a simple and cost-saving manner.

We have found that this object is achieved by producing tablets by melt calendering with the melt containing active ingredient being introduced between two sheets of the covering material into the calender molding rolls.

The present invention therefore relates to a process for the production of covered tablets by molding a melt containing active ingredient in a calender with two counter-rotating molding rolls which have on their surface mutually opposite depressions for receiving and molding the tablet composition, wherein the melt containing active ingredient is introduced between two sheets of the covering material into the molding rolls.

The tablets are produced starting from a mixture which contains one or more pharmaceutical active ingredients and one or more conventional ancillary substances and which becomes a paste or viscous liquid (thermoplastic), and can therefore be extruded, by melting or softening of at least one component.

The pharmaceutical mixture is then melted in a conventional way, preferably in an extruder, and fed to the molding calender as described, for example, in U.S. Pat. No. 4,880,585.

At the same time as the melt, two sheets which form the covering material are fed to the molding rolls, which are in contact along a surface line or are located at only a very small distance from one another, in such a way that the sheets are each located between molding roll and melt. Subsequently during the calendering the tablet composition is molded to the required tablet shape with, simultaneously, the part forming the covering of the tablets being cut out of the sheet and applied to the tablets. The temperatures prevailing on the molding rolls, which are generally from 50 to 150° C., result in softening of the sheet material and thus covering of the tablets. The sheet material melts at the edges of the tablets and thereby envelopes the tablets singly so that the tablet is completely and uniformly coated with the covering material.

If necessary, the covered tablets are subsequently subjected to a cooling process, for example in an air or cooling bath.

The process according to the invention has the advantage that the individual processes of granulation, tableting and coating, which take place discontinuously in conventional tablet production, are combined in a single process step which, moreover, takes place continuously. Furthermore, the application of the coating requires no additional energy input because it takes place at the same time as the tableting (in this case: calendering), which is anyway carried out at elevated temperatures.

In a preferred embodiment, sheets suitable for forming a film coating on the tablets are used so that film-coated tablets are obtained. The layer thickness of the film can be varied over a wide range. This is possible in the conventional spraying-on only by changing the process times (longer/shorter spraying time). The superiority of the novel process (saving of time) is particularly evident with thicker layers because these thick layers can be applied extremely rapidly and very uniformly. In general, sheets with a thickness of about 10 $\mu$m to 500 $\mu$m are used. It is possible to use sheets which differ in thickness so that there is a different thickness of film coating on the upper and lower halves of the tablet, which makes it possible specifically to influence, for example, the dissolution characteristics of the tablet in the gastrointestinal tract.

The sheet material can be selected from a wide range of materials. The only requirement is that the material is pharmaceutically acceptable. The sheet material can be chosen so that the resulting tablet dissolves in the gastric fluid or the resulting tablet has modified release of active ingredient, for example a tablet with enteric coating or a tablet with a prolonged action, for example a tablet of the sustained release type, prolonged release type, repeat release type or delayed release type.

Sheet materials which are suitable for producing such film-coated tablets and which rapidly dissolve in the acidic gastric fluid are, in particular, gelatin, polyvinyl alcohol, alkylcelluloses such as methylcelluloses, hydroxyalkylcelluloses such as hydroxyethyl-, hydroxypropyl- or hydroxypropylmethylcelluose, polyvinylpyrrolidone, certain acrylic resins such as copolymers based on dimethylaminoethyl methacrylate and methacrylates (Eudragit E) etc., alone or mixed with one another.

Examples of film formers which can be used according to the invention for coatings with modified release of active ingredient are alkylcelluloses such as ethylcellulose, polyvinyl esters such as polyvinyl acetate, certain acrylic resins such as copolymers based on methacrylic acid and methacrylate (Eudragit L and S), cellulose phthalates such as cellulose acetate phthalate or hydroxypropylmethylcellulose phthalate etc. The release characteristics can additionally be influenced by using sheets of different materials, it also being possible to use a plurality of sheets for covering one or both tablet halves.

When water-soluble sheets are used, thermoplastic polymers such as hydroxyalkylcelluloses, gelatin or acrylic resins have proven particularly suitable as sheet material. They can be used in a thickness of about 50 to 150 $\mu$m and, in this case, form a thin, very uniform water-soluble coating on the tablets.

The process according to the invention makes substantially aseptic production of tablets possible. The melting of the tablet composition and, if this takes place in an extruder, the intense input of shear energy into the product kills the microbes in the composition so that it can be fed as sterile product to the molding rolls. If sterilized polymer sheets are then used, and the melt calendering is carried out under aseptic conditions, for example with sterile air (laminar flow), the tablets are obtained in sterile form. The tablets can then be packed sterile in another process or, which is particularly preferred, blister-packed simultaneously with the molding of the tablets (see the statements hereinafter). In the latter case, the risk of contamination of the product with pathogenic microbes is considerably reduced by comparison with a conventional process with separate packaging.

The sheets can also according to the invention contain another active ingredient. This can be an active ingredient which is not compatible with one of the components in the tablet composition. The incompatible constituents are kept separate from one another in this way. The inclusion of an active ingredient in the sheet also makes it possible, however, to release an initial dose owing to the active ingredient contained in the sheet and then, with the actual tablet, to provide another single dose or maintenance of the drug concentration.

In another embodiment, the sheets used are those suitable for packaging the tablets. These are, in particular, water-insoluble thermoforming sheets, the preferred material being polyethylene, polypropylene, polyvinyl chloride, polyethylene terephthalate, polystyrene, aluminum or coated aluminum. The tablets are in this way immediately sealed in a blister pack. The separate packaging step which is otherwise customary is thus unnecessary and, moreover, it is possible in this way to pack the tablets aseptically in an extremely simple manner, especially when care is taken that the outer edges of the tablet strip are sealed airtight.

It has surprisingly emerged that there is not, as expected, vigorous adhesion of the hot tablet composition to the water-insoluble thermoforming sheet so that later removal of the tablets from the pack would be impeded or even impossible.

It has proven particularly advantageous for packaging the tablets to combine a molding roll with the depressions for receiving and molding the tablet composition with a smooth roll. This results in "half" tablets which are sealed in a blister pack which has on one side depressions for receiving the tablets and is closed on the other side with a smooth sheet which can be pulled off. In this case, an aluminum sheet or a sheet of coated aluminum has proven particularly expedient for closing the pack.

It may also prove to be expedient not to allow the packaged tablets to cool in air, as otherwise usual, but to provide a separate cooling step. Suitable for this purpose is a water bath, stream of cold air etc. This prevents the tablets in the pack cooling too slowly, which may lead to subsequent deformation of the tablets.

It is also possible to use the sheets for the film coating of the tablets and the sheets for the blister-packaging of the tablets simultaneously. In this case, the melt in the molding rolls is covered by the sheet for the film coating and simultaneously sealed in the packaging sheet. This makes it possible to carry out all the basic operations needed to produce the tablets, namely tableting, coating and packaging, in a single step which, moreover, takes place in a continuous manner. This is associated with enormous savings in cost.

In some cases it has proven expedient to coat the molding rolls or the sheets which are used, in particular the outer sides thereof, with a mold release agent in order to facilitate detachment of the tablets or the packaging from the molding rolls. Examples of suitable mold release agents are silicone resins, stearic acid, calcium or magnesium stearate, paraffin, cetyl alcohol or lecithins.

It is also possible using the process according to the invention to add further additives to the sheets in a simple manner. Examples of such additives are colored pigments, it being possible for the upper and lower sides of the tablets or the packaging to differ in color, masking flavors, plasticizers etc. It is also possible for one or both sheets to be printed, eg. with numbers, names etc., in order to ensure unambiguous identification of the tablets by the patients. This has been possible to date only by subsequent printing with ink jet printers.

The shape of the depressions and thus of the tablets can be chosen substantially as desired. Depressions which are elongate and in the shape of a segment of an ellipsoid, so that oblong tablets and lenticular tablets are obtained, are particularly expedient.

It is also possible, if required, to produce divisible tablets. For this purpose it is possible to provide a small rib, which is often in the micrometer range, on the bottom of the depressions, which leads to formation of the score in the finished tablets. However, it is preferable to use at least one molding roll in which the depressions are divided by at least one bar which extends essentially to the surface of the molding roll and forms the score.

The abovementioned mixtures for producing the tablets are, in particular, mixtures which contain pharmacologically acceptable polymers (with the glass transition temperature of the mixture being below the decomposition temperature of all the components of the mixture), for example polyvinylpyrrolidone (PVP), copolymers of N-vinylpyrrolidone (NVP) and vinyl esters, in particular vinyl acetate, copolymers of vinyl acetate and crotonic acid, partially hydrolyzed polyvinyl acetate, polyvinyl alcohol, ethylene/vinyl acetate copolymers, poly (hydroxyethyl methacrylate), copolymers of methyl methacrylate and acrylic acid, cellulose esters, cellulose ethers, in particular hydroxypropylcellulose, polyethylene glycol or polyethylene, preferably NVP copolymers with vinyl acetate, hydroxypropylcellulose and polyethylene glycols/polyethylene oxides. The K values (H. Fikentscher, Cellulose-Chemie 13 (1932) 58–64 and 71–74) of the polymers are in the range from 10 to 100, preferably 12 to 70, in particular 12 to 35, for PVP preferably 12–35, in particular 12–17.

The polymeric binder must soften or melt in the complete mixture of all the components in the range from 50 to 180, preferably 60 to 130° C., so that the composition can be extruded. The glass transition temperature of the mixture must therefore always be below 180, preferably below 130° C. It is if necessary reduced by conventional pharmacologically acceptable plasticizing ancillary substances such as long-chain alcohols, ethylene glycol, propylene glycol, trimethylolpropane, triethylene glycol, butanediols, pentanols, hexanols, polyethylene glycols, silicones, aromatic carboxylic esters (eg. dialkyl phthalates, trimellitic esters, benzoic esters, terephthalic esters) or aliphatic dicarboxylic esters (eg. dialkyl adipates, sebacic esters, azelaic esters, citric and tartaric esters) or fatty acid esters.

Examples of conventional pharmaceutical ancillary substances, whose total amount can be up to 100% by weight based on the polymer, are extenders such as silicates or diatomaceous earth, stearic acid or salts thereof, eg. the magnesium or calcium salt, methylcellulose, sodium carboxymethylcellulose, talc, sucrose, lactose, cereal or corn starch, potato flour, polyvinyl alcohol, also wetting agents, preservatives, disintegrants, absorbents, colorants, flavorings (cf., for example, H. Sucker et al. Pharmazeutische Technologie, Thieme-Verlag, Stuttgart 1978). The only condition for suitability thereof is adequate thermal stability.

Pharmaceutical active ingredients mean for the purpose of the invention all substances with a pharmaceutical effect and minimal side effects as long as they do not decompose under the processing conditions. The amount of active ingredient per dose unit and the concentration may vary within wide limits depending on the activity and rate of release. The only condition is that they suffice to achieve the desired effect. Thus, the concentration of active ingredient can be in the range from 0.1 to 95, preferably from 20 to 80, in particular 30 to 70, % by weight. It is also possible to use combinations of active ingredients. Active ingredients for the purpose of the invention are also vitamins and minerals, as well as crop treatment agents and insecticides.

The process according to the invention is suitable, for example, for processing the following active ingredients:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydroxide, benzocaine, benzoic acid, betamethasone, bezafibrate, biotin, biperiden, bisoprolol, prazosin, bromazepam, bromhexine, bromocriptine, budesonide, bufexamac, buflomedil, buspirone, caffeine, camphor, captopril, carbamazepine, carbidopa, carboplatin, carotenoids such as β-carotene or canthaxanthin, cefachlor, cefalexin, cefatroxil, cefazolin, cefixime, cefotaxime, ceftazidime, ceftriaxone, cefuroxime, celedilin, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, diltiazem, diphenhydramine, dipyridamole, dipyrone, disopyramide, domperidone, dopamine, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gemfibrozil, gentamicin, Ginkgo biloba, glibenclamide, glipizide, clozapine, Glycyrrhiza glabra, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, lipoic acid, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenylephrine, phenylpropanolamine, phenytoin, piroxicam, polymyxin B, povidone-iodine, pravastatin, prednisolone, bromocriptine, propafenone, propranolol, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulpiride, tamoxifen, tegafur, teprenone, terazosin, terbutaline, terfenadine, theophylline, thiamine, ticlopidine, timolol, tranexamic acid, tretinoin, triamcinolone acetonide, triamterene, trimethoprim, troxerutin, uracil, valproic acid, vancomycin, verapamil, vitamins $B_1$, $B_2$, $B_4$, $B_6$, $B_{12}$, $D_3$, E, K, folinic acid, zidovudine.

In a few cases, solid solutions may form. The term "solid solutions" is familiar to the skilled person, for example from the literature cited at the outset. In solid solutions of pharmaceutically active ingredients in polymers, the active ingredient is present in a molecular dispersion in the polymer.

The following examples illustrate the invention without restricting it.

EXAMPLE 1

A mixture of 60.0% by weight of Kollidon VA-64 (BASF) (polyvinylpyrrolidone copolymer with vinyl acetate (60:40)) and 40.0% by weight of lactose monohydrate was extruded in a twin screw extruder (ZSK-40, Werner+Pfleiderer) under the following conditions:

Temperatures:
  Shot 1: 80° C.
  Shot 2: 100° C.

Shot 3: 130° C.
Shot 4: 130° C.
Dies: 135° C.
Material throughput: 25 kg/h
Screw speed: 160 rpm The melt 5 was introduced together with two polypropylene sheets 2 about 300 micrometers thick (thermoforming blister sheet) into the molding calender with two molding rolls 1 which rotate in the direction of the arrows (useful widths of the molding rolls about 14 cm). The depressions 3 in the molding rolls 1 were designed so that oblong tablets (20×8.5 mm) 4 weighing about 1000 mg were molded from the melt. The material left the calender as strip of tablets packed in PP sheet. The tablets were not sealed singly in the sheet because the molding rolls of the calender were adjusted so that they were not in direct contact at any point (spacing about 0.1 mm). After cooling it was easy to remove the PP sheet as a strip about 14 cm wide (7 parallel rows of tablets on the molding roll) from the tablets. In no case was there adhesion of the melt to the PP sheet. It was possible to seal individual rows of tablets or the tablet strip across the whole width of the molding roll by subsequent welding of the outer edges (exclusion of air).

The calender and molding rolls useful for the present invention can be cooled or heated in a manner known per se and the optimum surface temperature of the rolls for the relevant processing step can be adjusted in this way.

We claim:

1. A process for the production of covered tablets by
   i) mixing one or more pharmaceutically active ingredients and one or more conventional ancillary substances to give a pharmaceutical mixture,
   ii) melting the pharmaceutical mixture to give a melted tablet composition, and
   iii) molding the melted tablet composition in a calender with counter-rotating molding rolls at least one of which molding rolls has on its surface depressions for receiving and molding the melted tablet composition,
   which process comprises
   a) introducing the melted tablet composition into the calender between two sheets of covering material, which covering material comprises a polymer selected from the group consisting of polyvinyl alcohol, alkylcellulose, hydroxy alkylcellulose, cellulose ester, carboxymethylcellulose, cellulose phthalate, polyvinyl pyrrolidone, polyvinyl ester, acrylic resins, and mixtures thereof,
   b) applying the covering material to the melted tablet composition simultaneously to the molding of the tablet composition into the required tablet shape,
   c) cutting out of the two sheets of covering material the parts forming the cover of the tablet simultaneously to the molding of the tablet composition into the required tablet shape,
   whereby the tablets are enveloped singly by the covering material to give a tablet completely and uniformly coated by the covering material.

2. The process of claim 1, wherein the coating material further comprises an active ingredient.

3. The process of claim 1, wherein the covering material provides an enteric coating or a coating for modified release of active ingredient.

4. The process of claim 1, wherein the molding rolls of the calender have different depressions.

5. The process of claim 1, wherein the calender has one molding roll with depressions and one smooth molding roll.

6. The process of claim 1, wherein the calender has at least one molding roll having depressions which are divided by at least one bar which extends essentially to the surface of the molding roll and forms a score to give divisible tablets.

7. The process of claim 1, wherein the calender has molding rolls which are coated with a mold release agent.

8. The process of claim 1, further comprising that the covered tablets are cooled for hardening.

9. The process of claim 1, wherein the different sheets of covering material differ from one another in their material or in their thickness.

10. The process of claim 1, wherein the coating material further comprises colored pigments or masking flavors or a release agent.

11. A process for the production of covered tablets by
    i) mixing one or more pharmaceutically active ingredients and one or more conventional ancillary substances to give a pharmaceutical mixture,
    ii) melting the pharmaceutical mixture to give a melted tablet composition, and
    iii) molding the melted tablet composition in a calender with counter-rotating molding rolls at least one of which molding rolls has on its surface depressions for receiving and molding the melted tablet composition,
    which process comprises
    a) introducing the melted tablet composition into the calender between two sheets of covering material, which covering material comprises polyethylene, polypropylene, polyvinyl chloride, polyethylene terephthalate, polystyrene, aluminum or coated aluminum,
    b) applying the covering material to the melted tablet composition simultaneously to the molding of the tablet composition into the required tablet shape,
    whereby the tablets are enveloped singly by the coating material to give tablets sealed in a blister pack.

12. The process of claim 11, wherein the different sheets of covering material differ from one another in their material or in their thickness.

13. The process of claim 11, wherein the coating material further comprises colored pigments or masking flavors or a release agent.

14. The process of claim 11, wherein the molding rolls of the calender have different depressions.

15. The process of claim 11, wherein the calender has one molding roll with depressions and one smooth molding roll.

16. The process of claim 11, wherein the calender has molding rolls which are coated with a mold release agent.

17. A process for the production of covered tablets by
    i) mixing one or more pharmaceutically active ingredients and one or more conventional ancillary substances to give a pharmaceutical mixture,
    ii) melting the pharmaceutical mixture to give a melted tablet composition, and
    iii) molding the melted tablet composition in a calender with counter-rotating molding rolls at least one of which molding rolls has on its surface depressions for receiving and molding the melted tablet composition,
    which process comprises
    a) introducing the melted tablet composition into the calender between two sets of two sheets of covering material,
       the inner set of sheets directly facing the melted tablet composition consisting of a covering material which comprises a polymer selected from the group consisting of polyvinyl alcohol, alkylcellulose, hydroxy alkylcellulose, cellulose ester, carboxymethylcellulose, cellulose phthalate, polyvinyl pyrrolidone, polyvinyl ester, acrylic resins, and mixtures thereof, and the outer set of sheets consisting of a covering material which comprises polyethylene, polypropylene, polyvinyl chloride, polyethylene terephthalate, polystyrene, aluminum or coated aluminum, b) applying the covering material of the inner set of sheets and the outer set of sheets to the melted tablet composition simultaneously to the molding of the tablet composition into the required tablet shape, c) cutting out of the two inner sheets of covering material the parts forming the cover of the tablet simultaneously to the molding of the tablet composition into the required tablet shape, whereby the tablets are enveloped singly by the coating material to give a tablet completely and uniformly coated by the covering material of the inner set of sheets, and d) applying the covering material of the outer set of sheets to the coated melted tablet composition simultaneously to the molding of the tablet composition into the required tablet shape, whereby the tablets are enveloped singly by the coating material of the outer set of sheets to give tablets sealed in a blister pack.

18. The process of claim 17, wherein the different sheets of covering material differ from one another in their material or in their thickness.

19. The process of claim 17, wherein the molding rolls of the calender have different depressions.

20. The process of claim 17, wherein the calender has one molding roll with depressions and one smooth molding roll.

* * * * *